(12) United States Patent
Fagot

(10) Patent No.: US 8,960,191 B2
(45) Date of Patent: Feb. 24, 2015

(54) POWDER INHALATION DEVICE

(75) Inventor: Christophe Fagot, Mezy (FR)

(73) Assignee: Aptar France SAS, Le Neubourg (FR)

( * ) Notice: Subject to any disclaimer, the term of this patent is extended or adjusted under 35 U.S.C. 154(b) by 500 days.

(21) Appl. No.: 13/003,488

(22) PCT Filed: Jul. 10, 2009

(86) PCT No.: PCT/FR2009/051374
§ 371 (c)(1),
(2), (4) Date: Jan. 10, 2011

(87) PCT Pub. No.: WO2010/004223
PCT Pub. Date: Jan. 14, 2010

(65) Prior Publication Data
US 2011/0120466 A1 May 26, 2011

(30) Foreign Application Priority Data

Jul. 11, 2008 (FR) ...................... 08 54756

(51) Int. Cl.
*A61M 15/00* (2006.01)
(52) U.S. Cl.
CPC ....... *A61M 15/0045* (2013.01); *A61M 15/0091* (2013.01); *A61M 15/0008* (2013.01); *A61M 15/0036* (2013.01); *A61M 15/004* (2013.01);
(Continued)
(58) Field of Classification Search
CPC .............. A61M 15/00; A61M 15/001; A61M 15/0005; A61M 15/0006; A61M 15/0008; A61M 15/002; A61M 15/0028; A61M 15/003; A61M 15/0031; A61M 15/0033; A61M 15/0035; A61M 15/0038; A61M 15/004; A61M 15/0041; A61M 15/0045; A61M 15/0046; A61M 15/0048; A61M 15/005; A61M 15/0051; A61M 15/0053; A61M 15/0058; A61M 15/0091
USPC ........................................ 128/203.19–203.21
See application file for complete search history.

(56) References Cited

U.S. PATENT DOCUMENTS 6,715,486 B2   4/2004  Gieschen et al.
2001/0027790 A1  10/2001  Gieschen et al.
(Continued)

FOREIGN PATENT DOCUMENTS

FR   2881118 A1   7/2006
FR   2909641 A1   6/2008
(Continued)

OTHER PUBLICATIONS

English translation of Pocock FR2909641.*

*Primary Examiner* — Rachel Young
(74) *Attorney, Agent, or Firm* — Sughrue Mion, PLLC

(57) ABSTRACT

A powder inhaler comprising: a body (10) that is provided with a dispenser orifice; at least one reservoir containing a dose of powder for dispensing; reservoir-opening means for opening a reservoir on each actuation; and a dispersion chamber (70) including an outlet (720) that is connected to said dispenser orifice, and an inlet (710) that is connected to said opening means and that receives the dose of powder from said open reservoir, said dispersion chamber (70) containing at least one movable element (75), such as a ball; the inhaler being characterized in that said dispersion chamber (70) includes a ball path (730) having a width that decreases from said inlet (710) in the direction of displacement of said at least one ball (75).

13 Claims, 2 Drawing Sheets

(52) U.S. Cl.
CPC ..... *A61M 15/0051* (2013.01); *A61M 2202/064* (2013.01)
USPC ............. 128/203.15; 128/203.21; 128/203.12

(56) References Cited

U.S. PATENT DOCUMENTS

2004/0123865 A1* 7/2004 Haikarainen et al. .... 128/203.15
2007/0251524 A1* 11/2007 Harmer et al. ........... 128/203.15

FOREIGN PATENT DOCUMENTS

| | | |
|---|---|---|
| GB | 2179260 A | 3/1987 |
| GB | 2375310 A | 11/2002 |
| WO | 2005/025550 A1 | 3/2005 |

* cited by examiner

POWDER INHALATION DEVICE

This application is a National Stage of International Application No. PCT/FR2009/051374 filed Jul. 10, 2009, which claims priority from French Patent Application No. 0854756 filed Jul. 11, 2008, the contents of all of which are incorporated herein by reference in their entirety.

The present invention relates to a powder inhaler, and more particularly to a dry-powder inhaler.

Inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. However, the inhaler is more difficult to use, since the user is obliged to load a capsule into the inhaler before each use. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation.

In order to dispense the powder in a finely pulverized form, document U.S. Pat. No. 6,715,486 describes a dispersion chamber containing one or more balls that are driven in rotation by the flow of air and powder directed from the open reservoir towards the dispenser orifice. The dispersion chamber breaks up clumps of the powder in satisfactory manner, and has a positive effect on flow resistance by reducing it. However, the effects of the ball-containing chamber are relatively sensitive to the orientation of the inhaler during inhalation, with properties of yield, variability, or resistance possibly being affected in the event of non-optimum orientation, corresponding to the inhaler being held other than vertically. Documents FR-2 909 641, WO 2005/025550, and GB-2 375 310 describe other prior-art devices.

An object of the present invention is to provide a fluid dispenser device, in particular a dry-powder inhaler, that does not have the above-mentioned drawbacks.

In particular, an object of the present invention is to provide such an inhaler that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide such an inhaler that guarantees good metering accuracy and good metering reproducibility on each actuation.

The present invention thus provides a powder inhaler comprising: a body that is provided with a dispenser orifice; at least one reservoir containing a dose of powder for dispensing; reservoir-opening means for opening a reservoir on each actuation; and a dispersion chamber including an outlet that is connected to said dispenser orifice, and an inlet that is connected to said opening means and that receives the dose of powder from said open reservoir, said dispersion chamber containing at least one movable element, such as a ball; said dispersion chamber including a ball path having a width that decreases from said inlet in the direction of displacement of said at least one ball.

Advantageously, the outer edge of said ball path is circular or elliptical.

Advantageously, the maximum width of said ball path is less than twice the diameter of a ball.

Advantageously, said ball path comprises a bottom surface that is substantially plane, an outer edge that is substantially circular, and an inner edge that is substantially circular and that is formed by a central profile, the central axis of said outer edge being offset from the central axis of said inner edge.

Advantageously, said dispersion chamber comprises a base portion and a cover portion.

Advantageously, said central profile is formed on the base portion.

Advantageously, said inlet is tangential in said dispersion chamber.

Advantageously, said dispersion chamber contains a plurality of balls, in particular six.

Advantageously, all of the balls have the same dimensions.

Advantageously, said opening means are perforator means comprising a needle that is adapted to perforate a reservoir on each actuation.

Advantageously, said opening means are controlled by the user inhaling, such that the reservoir is opened and emptied simultaneously, the powder driven by the inhalation flow passing through said dispersion chamber prior to being expelled through the dispenser orifice.

These characteristics and advantages and others of the present invention appear more clearly from the following detailed description, given by way of non-limiting example, and with reference to the accompanying drawings, and in which.

Figure 1:
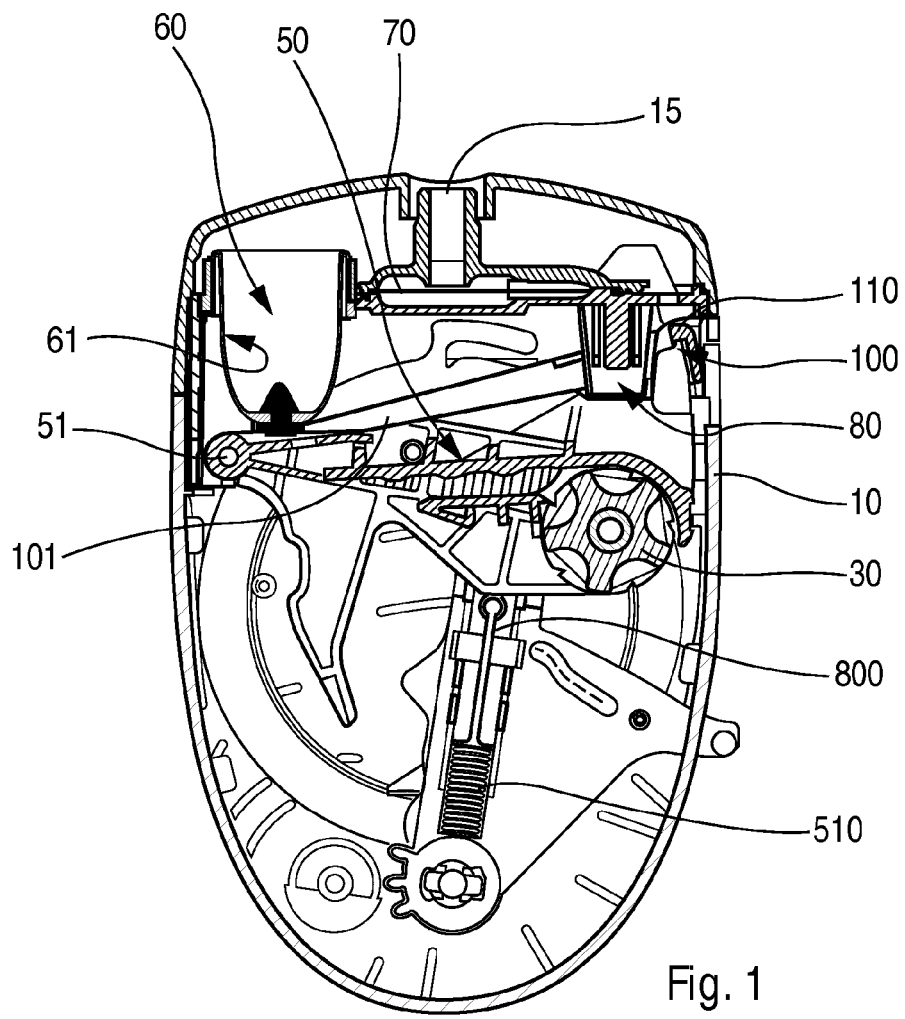
FIG. 1 is a diagrammatic section view of a powder inhaler.

FIG. 1 shows an advantageous variant embodiment of a dry-powder inhaler. The inhaler includes a body 10 on which there can be slidably or pivotally mounted two cap-forming portions (not shown) that are adapted to be opened so as to open and pre-stress the device. The body 10 can be approximately rounded in shape, but it could be of any other appropriate shape. The body 10 includes a mouthpiece or inhaler endpiece that defines a dispenser orifice 15 through which the user inhales while the device is being actuated. The caps can be opened by pivoting about a common pivot axis, but any other opening means can be envisaged for opening the device. In a variant, the device could include a single cover instead of two.

Inside the body 10 there is provided a strip (not shown) of individual reservoirs, also known as blisters, said strip being made in the form of a flexible elongate strip on which the blisters are disposed one behind another, in manner known per se. Before first use, the blister strip can be rolled-up inside the body 10, preferably in a storage portion, and first displacement means for displacing the strip 30 are provided for progressively unrolling the blister strip and for causing it to advance. Second displacement means 50, 51 are provided for bringing a respective blister or individual reservoir into a dispensing position each time the device is actuated. The strip portion including the empty reservoirs is advantageously adapted to be rolled-up at another location of said body 10, preferably a reception portion.

The inhaler includes reservoir opening means 80 (that are shown only in very diagrammatic manner in FIG. 1) preferably comprising perforator and/or cutter means for perforating and/or cutting the closure layer of the blisters. For example, the reservoir opening means advantageously comprise a needle that is preferably stationary relative to the body 10, and against which a respective blister is displaced on each actuation by the second displacement means. The blister is thus perforated by said needle which penetrates into said blister so as to expel the powder by means of the suction of the user inhaling.

The first displacement means are adapted to cause the blister strip to advance before and/or during and/or after each actuation of the device. The second displacement means are adapted to displace the reservoir to be emptied against said perforator and/or cutter means during actuation. The second displacement means can be urged, via stressing means 800, by a resilient element 510, such as a spring or any other equivalent resilient element, said resilient element being suitable for being pre-stressed while the device is being opened. Preferably, the first displacement means comprise an indexer wheel 30 that receives and guides the blisters. Turning the indexer wheel causes the blister strip to advance. In a particular angular position, a given reservoir is always in a position facing the opening means. The second displacement means can include a rotary support element 50 that turns about an axis of rotation 51, said indexer wheel 30 being rotatably mounted on said support element.

An actuation cycle of the device can be as follows. While the device is being opened, the two cap-forming lateral portions are moved apart by pivoting on the body in order to open the device and thus pre-stress the device. In this position, the indexer wheel cannot be displaced towards the needle, since the second displacement means are held by appropriate blocking means 100, 110. Preferably, it is while the user is inhaling through the mouthpiece that the blocking means are unblocked, thereby causing said support element 50 to pivot and thus said indexer wheel 30 to move towards the needle, and thereby causing a reservoir to be opened.

In use, the optimum orientation of the inhaler corresponds to a position that is substantially vertical, with the dispenser orifice 15 directed upwards, as shown in FIG. 1.

As explained above, it is desirable for the opening means to be actuated by the user inhaling. In order to trigger the reservoir opening means by inhalation, an inhalation trigger system can be provided that advantageously comprises a unit 60 that is displaceable and/or deformable under the effect of inhalation, the unit being adapted to release the blocking means 100, 110, e.g. via a rod 101. The unit advantageously comprises a deformable air-chamber 61. Inhalation by the user causes said deformable air-chamber to deform, thereby making it possible to release said blocking means and to enable the displacement of the second displacement means, and therefore of a respective reservoir towards its opening position. The reservoir is therefore opened only on inhalation, such that it is emptied simultaneously. Thus, there is no risk of any of the dose being lost between opening the reservoir and emptying it.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

Figure 3:
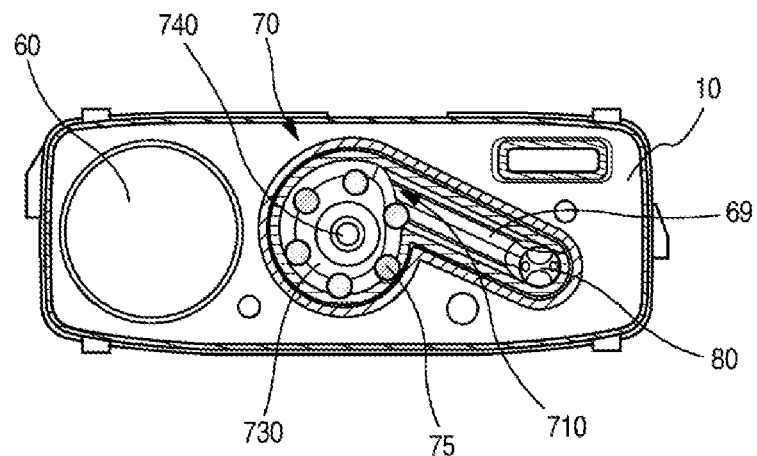
FIG. 3 is a view similar to the view in FIG. 2, in plan cross-section.
Figure 4:
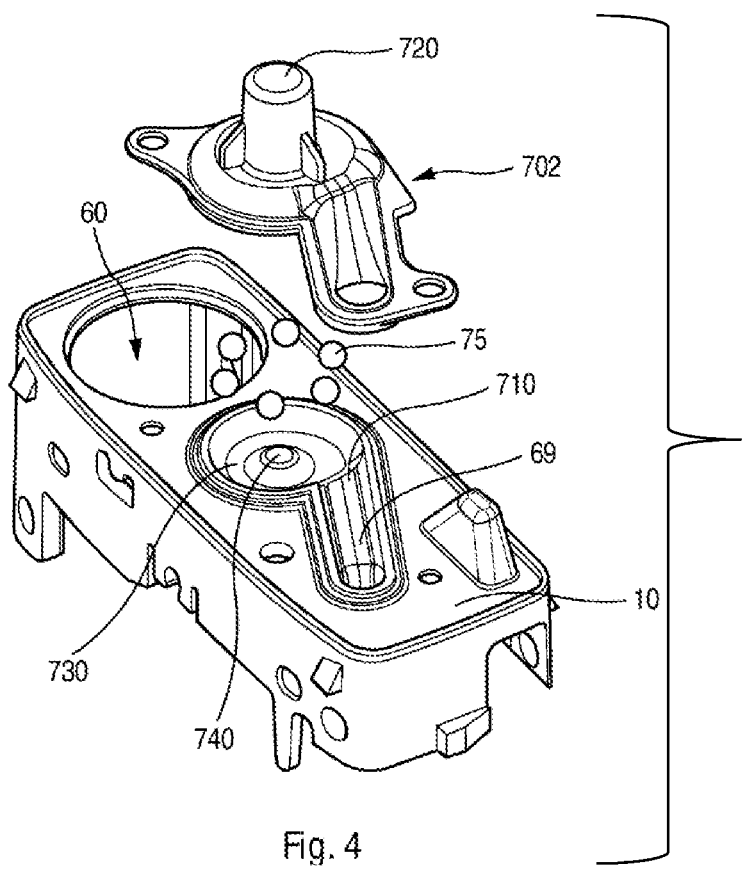
FIG. 4 is a diagrammatic exploded perspective view of the portion of the inhaler in FIGS. 2 and 3.

The inhaler further includes a dispersion chamber 70 for receiving the dose of powder after a respective reservoir has been opened. The dispersion chamber 70 is provided with at least one ball 75, preferably six balls, as can be seen in FIGS. 3 and 4, the ball(s) moving inside said chamber 70 during inhalation, so as to improve the dispensing of the air and powder mixture after a reservoir has been opened, so as to increase the effectiveness of the device.

Figure 2:
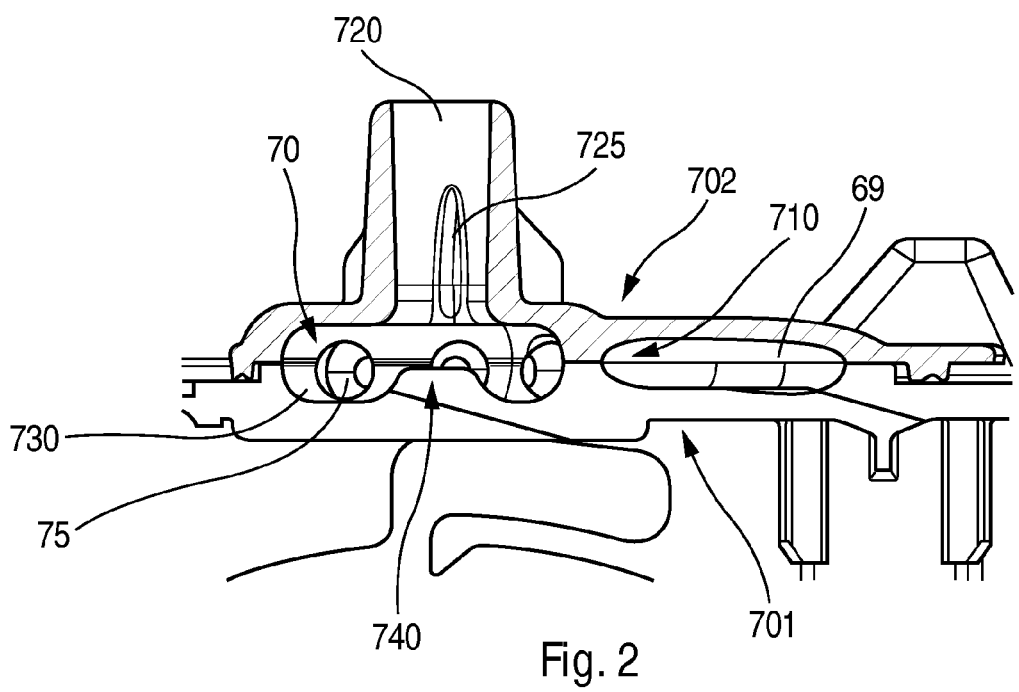
FIG. 2 is a diagrammatic side section view of a portion of the FIG. 1 inhaler in an advantageous embodiment of the invention.

The dispersion chamber 70 is preferably circular or elliptical in shape, with an inlet 710 that is preferably tangential in said chamber, and an outlet 720 that is perpendicular, preferably oriented along a vertical axis that passes approximately through the center of said dispersion chamber 70. Preferably, the dispersion chamber 70 is formed of two portions, a base portion 701 and a cover portion 702 that are assembled together during assembly of the device. Advantageously, the outlet 720 is formed on the cover portion 702, while the inlet 710 is formed by both portions, namely the base portion 701 and the cover portion 702. The dispersion chamber 70 includes a ball path 730 that preferably follows the shape of said dispersion chamber approximately, namely a circle or an ellipse as appropriate. The ball path 730 advantageously comprises a bottom surface that is substantially plane, and two side edge walls that are curved so as to enable the balls to move rapidly. Preferably, the ball path 730 is defined radially inside by a central projection 740 that is preferably formed on the base portion 701. In particular, this is advantageous for assembly, the balls 75 positioning themselves automatically in the ball path 730 prior to fastening the cover portion 702 on the base portion 701. In a variant, an appropriate profile could be provided on the cover portion, as shown in FIG. 1. The central profile 740 is preferably disposed facing the outlet 720 of the dispersion chamber 70, as can be seen in FIG. 2. The outlet 720 preferably includes one or more restrictions 725 inside the channel, so as to prevent the ball(s) 75 provided in the dispersion chamber 70 from being expelled. This is a safety measure in the event of a ball 75 escaping from the ball path, e.g. during assembly. In the preferred embodiment, the dispersion chamber 70 includes a plurality of balls 75, preferably six, and the balls preferably have the same dimensions. In order to enable the balls 75 to move rapidly along the ball path 730, the width of the ball path is greater than the diameter of the balls (or greater than the diameter of the largest ball if the balls have different dimensions). Ball paths 730 can be provided that are wide enough to enable two balls to be disposed side by side in said ball path, but the ball path 730 is preferably designed to enable the passage of only one ball at a time. In this advantageous embodiment, the width of the ball path 730 is thus less than twice the diameter of the balls. As can be seen in FIGS. 3 and 4, the inlet 710 connects the dispersion chamber 70 to the perforator element 80 via a channel 69. In the variants shown, the balls 75 turn in the counter-clockwise direction, but naturally the channel 69 that leads to the inlet of the dispersion chamber could be disposed in another orientation, with the balls 75 turning in the clockwise direction inside the dispersion chamber. Similarly, the inlet 710 is not necessarily completely tangential, and it could even be desirable to provide an inlet 710 that is offset a little relative to the tangent.

In an embodiment of the invention, the width of the ball path 730 decreases in the direction of displacement of the balls, starting from the inlet 710 of the dispersion chamber. The ball path 730 thus has a "snail" or "spiral" shape that tapers on going away from said air inlet 710. This has the effect of accelerating the flow of air in said ball path 730, and thus of reducing the amount of powder that is retained on the side walls of said dispersion chamber, in particular in the zones at a distance from the inlet 710, in the direction of flow. In the embodiment shown in FIGS. 3 and 4, the direction of rotation is counter-clockwise, but the air inlet 710 could be oriented in some other way, with an opposite direction of rotation, i.e. in the clockwise direction for the balls. In this second event, naturally the tapering of the width is also reversed compared to the tapering shown in FIGS. 3 and 4.

Advantageously, the decreasing width of the ball path 730 is formed by offsetting the central profile or projection 740 relative to the axis of symmetry of the dispersion chamber 70. The substantially-plane bottom surface of the ball path 730 thus tapers, as can be seen in FIGS. 3 and 4. Thus, the plane bottom surface of the ball path 730 tapers, the outer edge being circular, the inner edge being circular, and the central axis of said outer edge being offset from the central axis of said inner edge. As can be seen in FIGS. 2 and 4, the inner and outer edges are curved so as to form a rounded ball path.

After inhalation, when the user closes the device, all of the components return to their initial, rest position. The device is thus ready for a new utilization cycle.

The present invention therefore makes it possible to provide a dry-powder inhaler that performs the following functions:

a plurality of individual doses of powder stored in individual sealed reservoirs, e.g. 30 or 60 doses stored on a rolled-up strip;

the powder is released by perforation that is achieved by the user inhaling, the blister being perforated by means of an inhalation detector system that is coupled to a pre-stressed release system;

appropriately-shaped drive means that are engaged with blisters so as to displace the blister strip on each actuation, and to bring a new reservoir into a position in which it is to be opened by appropriate opening means;

an effective dispersion of the powder prior to it being expelled, so as to limit the amount of powder that is retained, and so as to guarantee good metering accuracy and reproducibility on each actuation, even when the orientation of the inhalation is not optimum.

Other functions are also provided by the device of the invention as described above. It should be observed that the various functions, even if they are shown as being provided simultaneously on the various embodiments of the inhaler, could be implemented separately. In particular, the inhalation trigger mechanism could be used regardless of the type of reservoir opening means, regardless of the use of a dose indicator, regardless of the way in which the individual reservoirs are arranged relative to one another, regardless of the shape of the dispersion chamber, etc. The cocking means and the inhalation trigger system could be made in some other way. The same applies for other component parts of the device.

Various modifications can also be envisaged by a person skilled in the art, without going beyond the ambit of the present invention, as defined by the accompanying claims.

The invention claimed is:

1. A powder inhaler comprising: a body that is provided with a dispenser orifice; at least one reservoir containing a dose of powder for dispensing; reservoir-opening means for opening a reservoir on each actuation; and a dispersion chamber including an outlet that is connected to said dispenser orifice, and an inlet that is connected to said opening means and that receives the dose of powder from said open reservoir, said dispersion chamber containing at least one movable element; wherein said dispersion chamber includes a ball path that defines displacement of said at least one moveable element;

wherein the ball path comprises a bottom surface that is substantially planar, an outer edge that is substantially circular, and an inner edge that is substantially circular and that is formed by a central profile, a central axis of said outer edge being offset from the central axis of said inner edge, wherein a width of said substantially plane bottom surface of the ball path narrows in a direction of movement of the ball along the ball path away from the air inlet.

2. A device according to claim 1, wherein the outer edge of said ball path is circular or elliptical.

3. A device according to claim 1, wherein a maximum width of said ball path is less than twice the diameter of a movable element.

4. A device according to claim 1, wherein said dispersion chamber comprises a base portion and a cover portion.

5. A device according to claim 1, wherein said central profile is formed on the base portion.

6. A device according to claim 1, wherein said inlet is tangential in said dispersion chamber.

7. A device according to claim 1, wherein said dispersion chamber contains a plurality of movable elements.

8. A device according to claim 7, wherein all of the movable elements have the same dimensions.

9. A device according to claim 1, wherein said opening means are perforator means comprising a needle that is adapted to perforate a reservoir on each actuation.

10. A device according to claim 1, wherein said opening means are controlled by a user inhaling, such that a reservoir is opened and emptied simultaneously, the powder driven by an inhalation flow passing through said dispersion chamber prior to being expelled through the dispenser orifice.

11. The device according to claim 1, wherein the at least one movable element is a ball.

12. The device according to claim 1, wherein said dispersion chamber contains six movable elements.

13. A powder inhaler, comprising:
a body provided with a dispenser orifice;
a reservoir containing a dose of powder for dispensing;
a perforator or cutter configured to open the reservoir upon actuation; and
a dispersion chamber including an outlet that is connected to the dispenser orifice, and an inlet that is connected to the perforator or cutter and that receives the dose of powder from the opened reservoir;
the dispersion chamber comprises a movable element;
the dispersion chamber comprising a generally spiral planar path along which the movable element moves, the planar path having a width that continuously decreases as the path extends away from the inlet and along the spiral.

* * * * *